(12) United States Patent
Li

(10) Patent No.: US 7,570,568 B2
(45) Date of Patent: Aug. 4, 2009

(54) HIGH PERFORMANCE DVD WRITING CURRENT CIRCUIT

(75) Inventor: Eric Li, Milpitas, CA (US)

(73) Assignee: Silicon Core Technology, Inc., Milpitas, CA (US)

( * ) Notice: Subject to any disclaimer, the term of this patent is extended or adjusted under 35 U.S.C. 154(b) by 588 days.

(21) Appl. No.: 10/585,399

(22) PCT Filed: Jan. 13, 2005

(86) PCT No.: PCT/US2005/001233

§ 371 (c)(1),
(2), (4) Date: Jul. 5, 2006

(87) PCT Pub. No.: WO2005/069863

PCT Pub. Date: Aug. 4, 2005

(65) Prior Publication Data

US 2009/0028008 A1    Jan. 29, 2009

Related U.S. Application Data

(60) Provisional application No. 60/536,535, filed on Jan. 15, 2004.

(51) Int. Cl.
*G11B 7/00* (2006.01)
(52) U.S. Cl. .................... 369/116; 369/53.26
(58) Field of Classification Search .............. None
See application file for complete search history.

(56) References Cited

U.S. PATENT DOCUMENTS

| | | | |
|---|---|---|---|
| 5,502,702 A | 3/1996 | Nakajo | |
| 5,732,055 A | 3/1998 | Masaki et al. | |
| 6,115,338 A | 9/2000 | Masaki et al. | |
| 6,148,428 A | 11/2000 | Welch et al. | |
| 6,172,951 B1 | 1/2001 | Ohba | |
| 6,317,405 B1 | 11/2001 | Arai | |
| 6,381,724 B1 | 4/2002 | Welch et al. | |
| 6,388,970 B1 | 5/2002 | Iizuka | |
| 6,414,932 B1 | 7/2002 | Kaku et al. | |
| 6,441,661 B1 | 8/2002 | Aoki et al. | |
| 6,466,732 B1 | 10/2002 | Kimura et al. | |
| 6,487,154 B1 | 11/2002 | Kurebayashi et al. | |
| 6,504,807 B2 | 1/2003 | Harvey et al. | |
| 6,636,472 B2 | 10/2003 | Kurebayashi et al. | |

(Continued)

FOREIGN PATENT DOCUMENTS

JP      2000216470 A      8/2000

(Continued)

*Primary Examiner*—Paul Huber
(74) *Attorney, Agent, or Firm*—Donald E. Schreiber

(57) ABSTRACT

A writing current circuit (42) supplies a controlled electrical current to a laser diode (34) for recording data swiftly onto a DVD (16). A plurality of thermometer code registers (52) respectively store numerical values. A current control register (58) receives a numerical value from one of the thermometer code registers (52). Serial data specifies a sequence in which individual thermometer code registers (52) supply values to the current control register (58) thereby causing the writing current circuit (42) to supply a particular electrical current waveform to the laser diode (34). A plurality of current sources (62) respectively receive a single output signal from the current control register (52) which activates or deactivates individual current sources (62) for supplying a particular quantity of current to the laser diode (34).

10 Claims, 5 Drawing Sheets

U.S. PATENT DOCUMENTS

| | | |
|---|---|---|
| 6,654,328 B2 | 11/2003 | Kaku et al. |
| 6,657,933 B2 | 12/2003 | Wong et al. |
| 6,657,936 B2 | 12/2003 | Harvey et al. |
| 6,691,203 B1 | 2/2004 | Chen et al. |
| 6,704,263 B1 | 3/2004 | Nijboer et al. |
| 6,721,261 B2 | 4/2004 | Kaku et al. |
| 6,775,217 B1 | 8/2004 | Kato et al. |
| 6,901,039 B1 | 5/2005 | Sugie et al. |
| 2002/0006085 A1 | 1/2002 | Kamatani |
| 2002/0061040 A1 | 5/2002 | Ishiwata et al. |
| 2002/0080701 A1 | 6/2002 | Nakajima |
| 2002/0098806 A1 | 7/2002 | Park |
| 2002/0105880 A1 | 8/2002 | Lee et al. |
| 2002/0150018 A1 | 10/2002 | Kelly et al. |
| 2002/0190779 A1 | 12/2002 | Aiba et al. |
| 2003/0048712 A1 | 3/2003 | Bakx et al. |
| 2003/0048821 A1 | 3/2003 | Iimura et al. |
| 2003/0072232 A1 | 4/2003 | Kwon |
| 2003/0142600 A1 | 7/2003 | Kamatani |
| 2003/0151994 A1 | 8/2003 | Tasaka et al. |
| 2003/0185127 A1 | 10/2003 | Chen et al. |
| 2003/0227844 A1 | 12/2003 | Chen et al. |
| 2004/0032806 A1 | 2/2004 | Chiou |
| 2004/0052173 A1 | 3/2004 | Hsu |

FOREIGN PATENT DOCUMENTS

| | | |
|---|---|---|
| JP | 2001043531 A | 2/2001 |
| WO | WO 02/51009 A1 | 6/2002 |

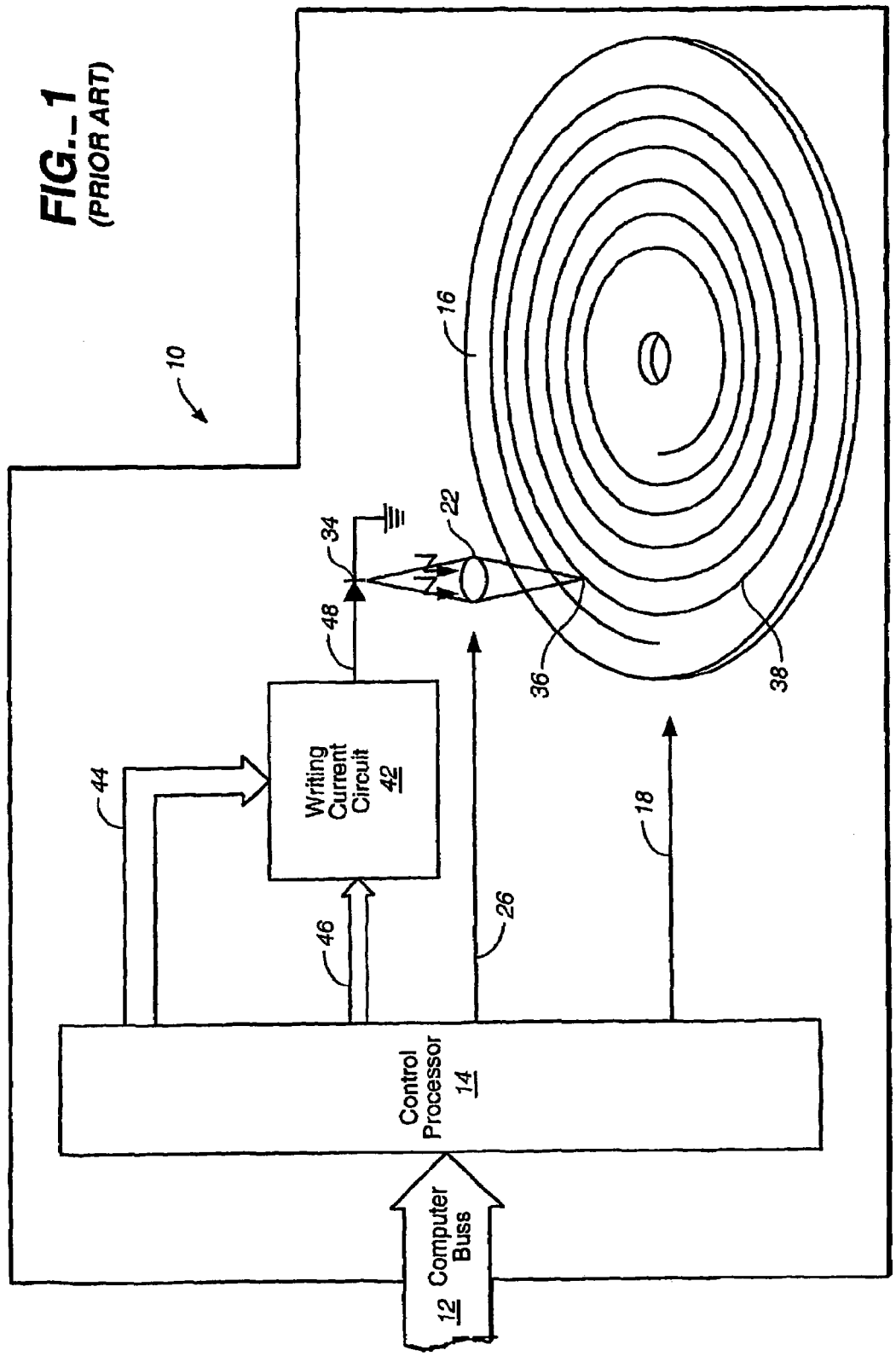
FIG._1
(PRIOR ART)

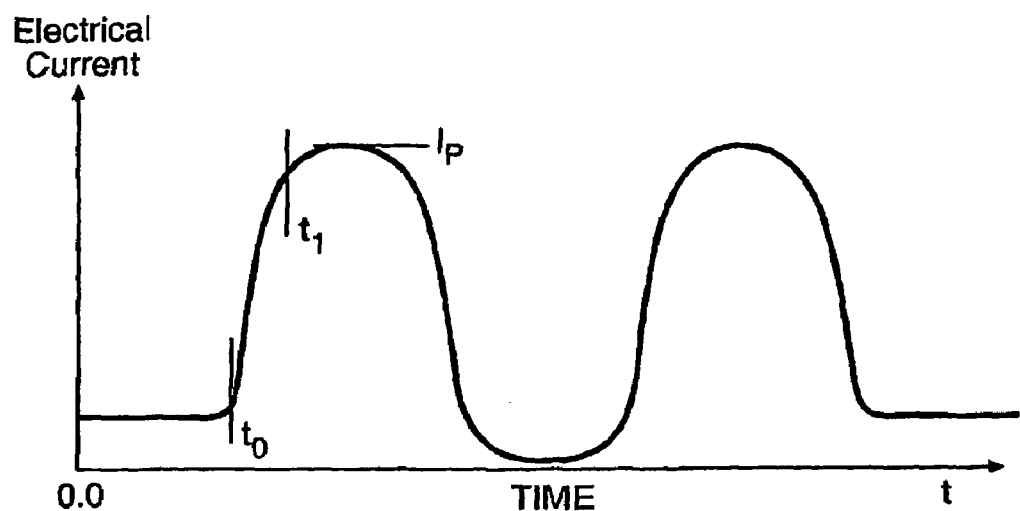
FIG._2
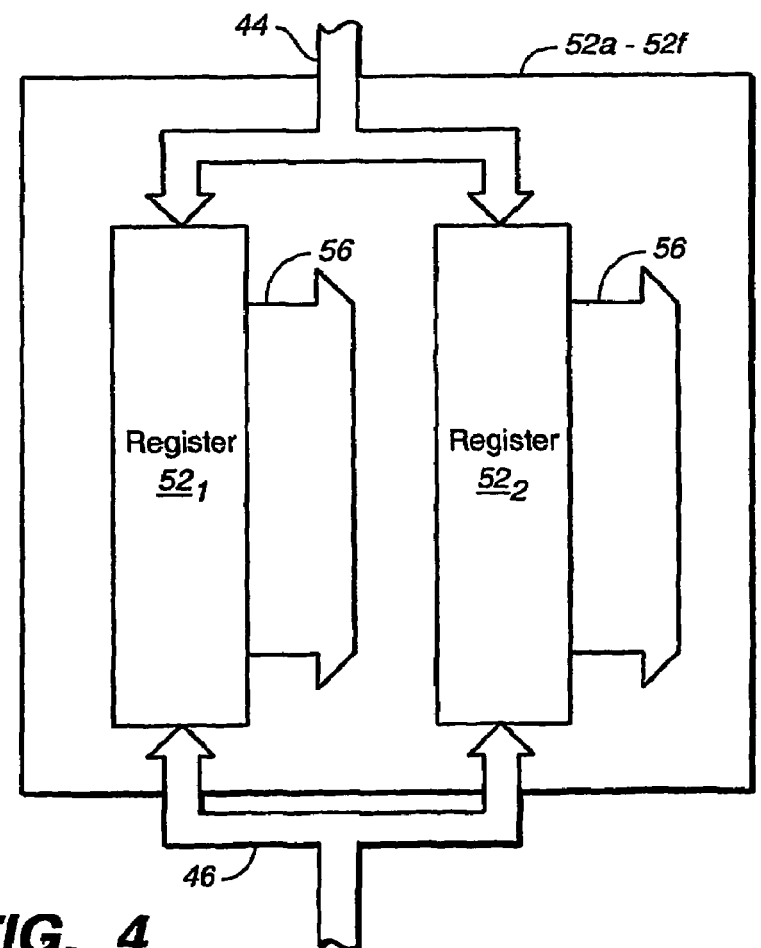
FIG._4

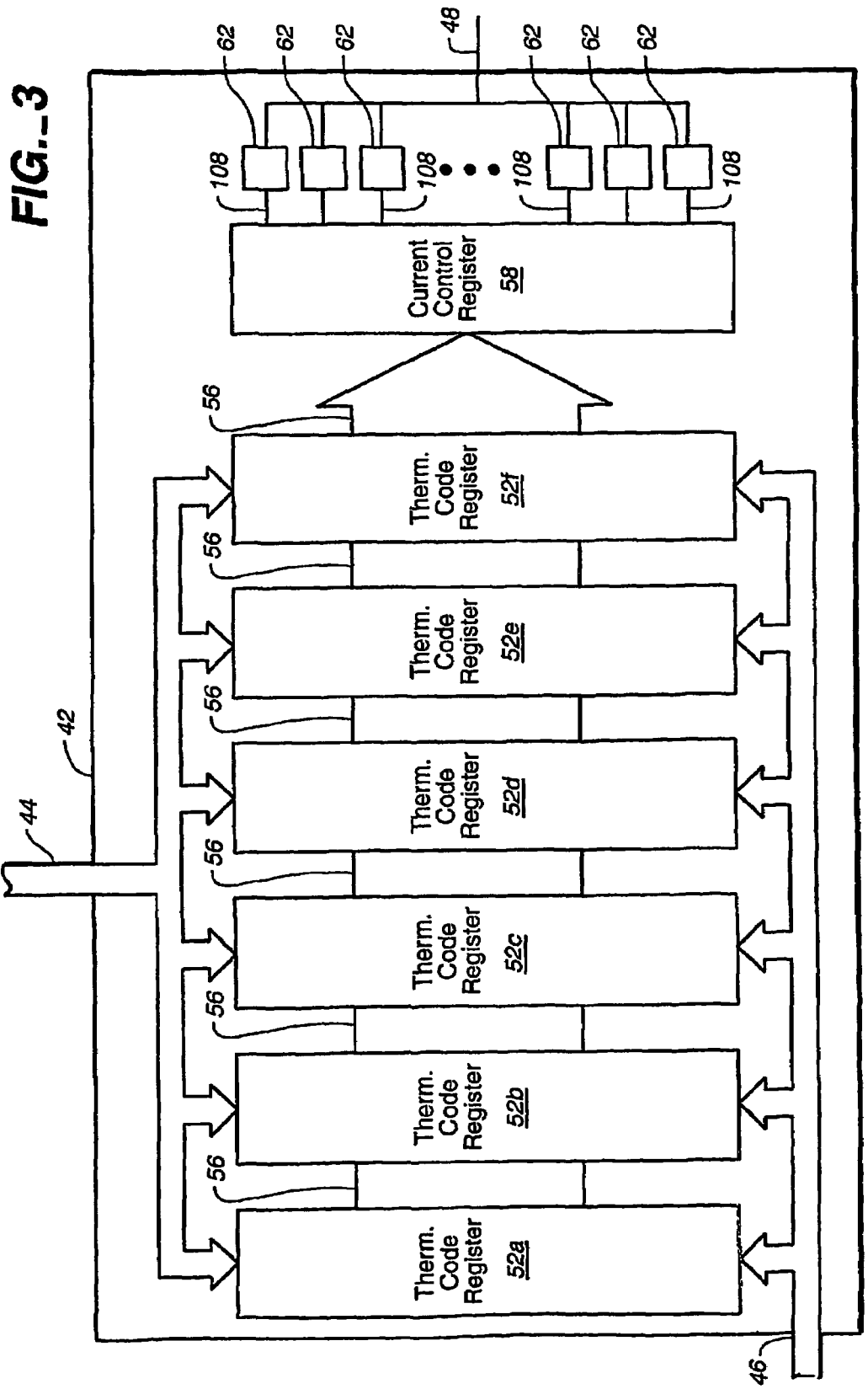
FIG._3

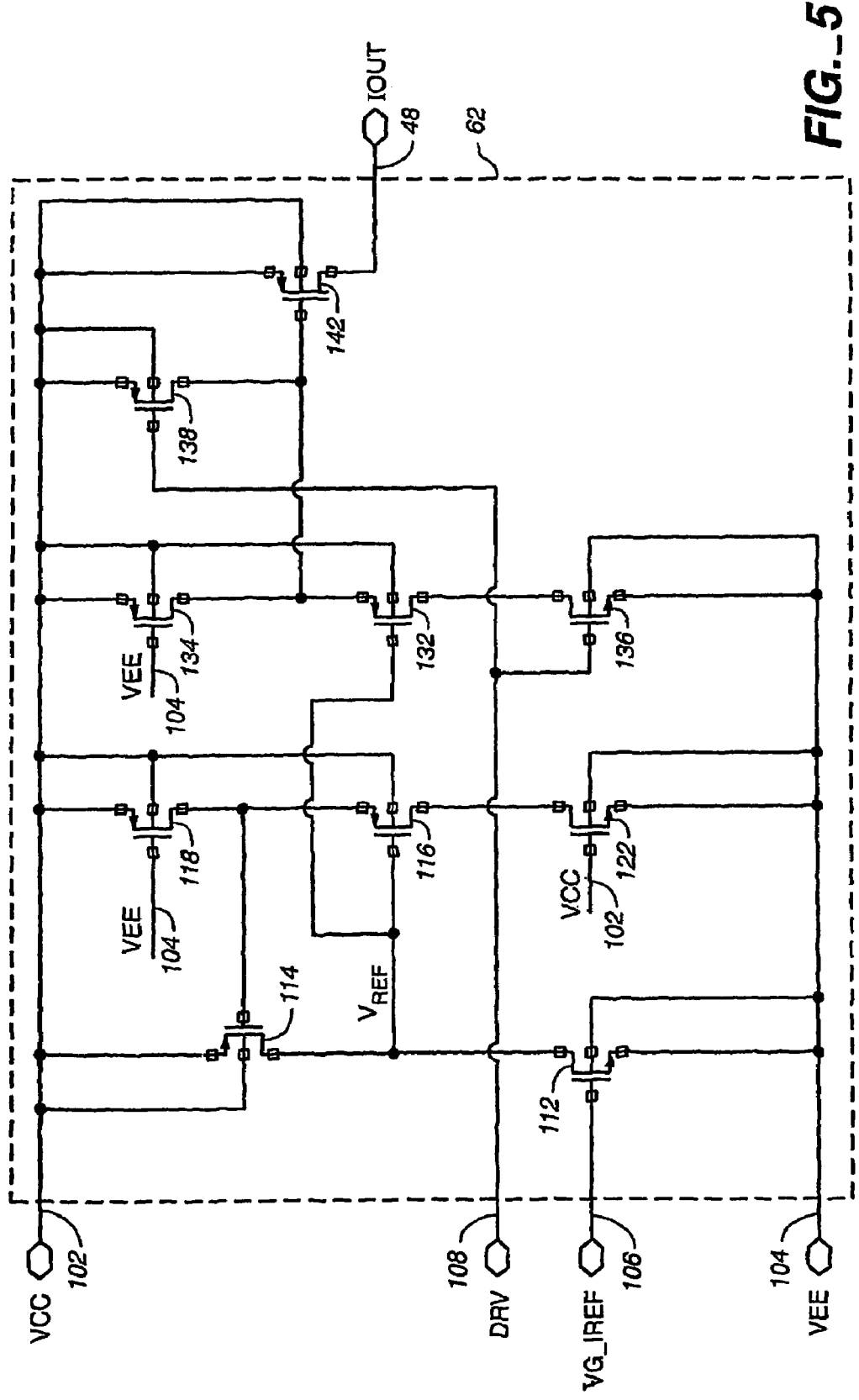
FIG._5

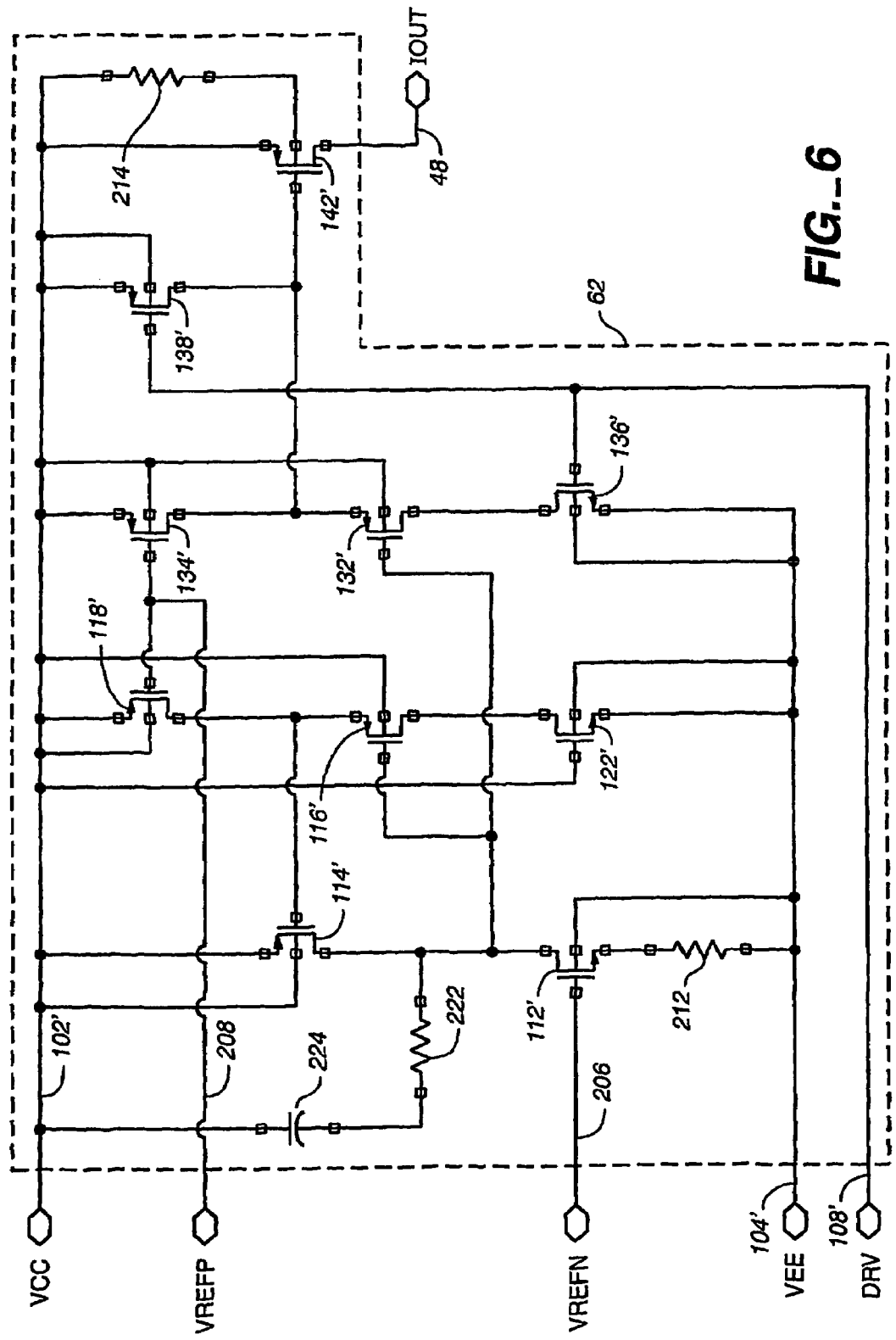
FIG._6

HIGH PERFORMANCE DVD WRITING CURRENT CIRCUIT

This application is a 371 of PCT/US2005/001233, filed Jan. 13, 2005, which claims benefit of 60/536,535, filed Jan. 15, 2004.

TECHNICAL FIELD

The present invention relates generally to optical digital data recording, and, more particularly, to a circuit that permits writing Digital Video Discs ("DVDs") swiftly.

BACKGROUND ART

The block diagram of FIG. 1 depicts selected portions of a prior art drive referred to by the general reference character 10. FIG. 1 particularly illustrates those portions of the drive 10 which adapt it for recording digital data on a Compact Disc ("CD") or DVD.

The drive 10, which is usually incorporated into a digital computer, exchanges digital data with other portions of the digital computer via a computer bus 12. For purposes of the present invention, the drive 10 may be understood conceptually as including a control processor 14, although drives 10 may be actually constructed in various other different ways. Responsive to commands which the drive 10 receives via the computer bus 12, the control processor 14, among other things, supervises:

1. rotation of a CD or DVD 16 received into the drive 10 indicated in FIG. 1 by an arrow 18; and
2. operation of an optical subsystem 22 indicated in FIG. 1 by an arrow 26.

The optical subsystem 22 focuses light, generated by a laser diode 34, to a spot 36 that is located along a track 38 which spirals inward across the surface of the CD or DVD 16. The control processor 14 operates in fundamentally the same manner for supervising rotation of the CD or DVD 16 and operation of the optical subsystem 22 both while the drive 10 records digital data onto the CD or DVD 16, and while the drive 10 reads previously recorded data from the CD or DVD 16.

When recording data onto the CD or DVD 16, the control processor 14 may be understood as supplying to an integrated circuit ("IC") writing current circuit 42:

1. write control data via a writing control bus 44; and
2. serial data for recording along the spiral track 38 via lines that are included in a recorded data bus 46.

In turn, the writing current circuit 42 supplies a controlled electrical current to the laser diode 34 via a current output line 48 to generate a temporally changing light beam which the optical subsystem 22 focuses at the spot 36 on the track 38. Heating of the CD or DVD 16 due to the beam of light impinging at the spot 36 alters the physical properties of the CD or DVD 16 thereby recording along the track 38 the digital data which the writing current circuit 42 receives via the recorded data bus 46.

While recording onto the CD or DVD 16, the energy of the light beam generated by the laser diode 34 must be controlled to heat the CD or DVD 16 at the spot 36 to a precise temperature needed to change the physical properties of the CD or DVD 16. Consequently, the electrical current which the writing current circuit 42 supplies to the laser diode 34 must be precisely controlled responsive to various different recording conditions which include:

1. the physical characteristics of various different types of CDs or DVDs 16 that may be loaded into the drive 10;
2. the speed at which the CD or DVD 16 rotates; and
3. the location of the spot 36 along the spiral track 38.

The waveform diagram of FIG. 2 depicts how electrical current supplied by the writing current circuit 42 to the laser diode 34 varies during recording of a single bit of digital data onto the CD or DVD 16. Depending upon specific recording conditions, in conventional drives 10 the electrical current which the writing current circuit 42 supplies to the laser diode 34 when recording onto a CD at 52× increases from a nominal value of approximately ten milliamperes ("ma") at time $t_0$ to as much as several hundred ma at time $t_1$, a time interval of approximately one nanosecond. The maximum electrical current supplied to the laser diode 34, $I_P$, may be as great as 350 ma. An electrical current supplied to the laser diode 34 which increases too swiftly or overshoots excessively can destroy the CD or DVD 16.

A significant performance difference required for a writing current circuit 42 adapted for recording digital data onto a CD and a writing current circuit 42 adapted for recording digital data onto a DVD arises from the smaller size spot 36 written on DVDs. The size of the spot 36 recorded onto DVDs is approximately one-seventh (1/7) the size of the spot 36 recorded onto CDs. Consequently, for the same rotation speed of the CD or DVD 16, data must be written seven (7) times faster when recording onto a DVD than when recording onto a CD. Correspondingly, for the same rotation speed the interval during which the light beam heats the spot 36 while writing a single bit of digital data onto a DVD is only one-seventh (1/7) of the interval for writing digital data onto a CD. Therefore, for media having similar physical properties the beam of light produced by the laser diode 34 must heat a DVD seven (7) times faster than the beam of light used for recording digital data onto a CD.

DISCLOSURE OF INVENTION

An object of the present invention is to provide a writing current circuit that permits writing digital data more swiftly.

Another object of the present invention is to provide a writing current circuit that supplies to the laser diode of an optical recording device an electrical current that changes smoothly.

Another object of the present invention is to provide a writing current circuit that supplies to the laser diode of an optical recording device an electrical current controllably.

Another object of the present invention is to provide a writing current circuit that supplies the laser diode of an optical recording device with an electrical current that exhibits the same rise time and same overshoot regardless of the amount of electrical current being supplied thereto.

Briefly, in one aspect the present invention is a writing current circuit adapted for supplying a controlled electrical current to a laser diode included in a drive for recording digital data swiftly onto a DVD.

The writing current circuit receives from a control processor included in the drive both:

a. write control digital data via a writing control bus which interconnects the writing current circuit and the control processor; and
b. serial digital data to be recorded on the DVD via a recorded data bus which also interconnects the writing current circuit and the control processor.

The writing current circuit includes a plurality of thermometer code registers. Each thermometer code register stores a numerical value which specifies a particular quantity of electrical current which the writing current circuit may supply to the laser diode. The thermometer code registers respectively receive the stored numerical values from the control processor via the writing control bus.

The writing current circuit also includes a current control register which receives a numerical value from a selected one of the thermometer code registers via a thermometer code transfer bus that interconnects the current control register with all of the thermometer code registers. Serial digital data received by the thermometer code registers via the recorded data bus specify a sequence in which individual thermometer code registers supply respective numerical values to the current control register via the thermometer code transfer bus. In this way, the writing current circuit can supply a particular electrical current waveform to the laser diode.

Lastly, the writing current circuit includes a plurality of separate current sources. Each of the current sources receives a single output signal from the current control register. When the output signal respectively received by each current source is in a first state, the current source is activated for supplying a particular quantity of electrical current to the laser diode. When the output signal respectively received by each current source is in a second state, the current source is deactivated for supplying the particular quantity of electrical current to the laser diode.

In another aspect, the present invention is a method for operating a writing current circuit that is adapted for supplying a controlled electrical current to a laser diode included in a drive for recording digital data onto a DVD swiftly.

The method includes the step of the writing current circuit providing a plurality of thermometer code registers for respectively receiving and storing a numerical value which specifies a particular quantity of electrical current which the writing current circuit may supply to the laser diode. The method also includes the step of the writing current circuit receiving from a control processor included in the drive both:

a. write control digital data which includes numerical values which are received into and stored in the thermometer code registers; and
  b. serial digital data to be recorded on the DVD.

The method includes the step of the writing current circuit further providing a current control register for receiving a numerical value from a selected one of the thermometer code registers. The method further includes the step of the writing current circuit receiving from the control processor serial digital data for specifying a sequence in which individual thermometer code registers supply respective numerical values to the current control register, whereby the writing current circuit supplies a particular electrical current waveform to the laser diode.

Finally the method includes the writing current circuit providing a plurality of separate current sources for respectively receiving a single output signal from the current control register. The output signal respectively received by each current source:

a. when in a first state activating the receiving current source for supplying a particular quantity of electrical current to the laser diode; and
  b. when in a second state deactivating the receiving current source for supplying the particular quantity of electrical current to the laser diode.

These and other features, objects and advantages will be understood or apparent to those of ordinary skill in the art from the following detailed description of the preferred embodiment as illustrated in the various drawing figures.

BRIEF DESCRIPTION OF DRAWINGS

FIG. 1 is a block diagram that depicts selected portions of a prior art drive adapted for writing CDs or DVDs;

FIG. 2 is a waveform diagram illustrating electrical current which a writing current circuit supplies to a laser diode while writing a single bit of digital data;

FIG. 3 is a block diagram depicting an IC writing current circuit in accordance with the present invention;

FIG. 4 is a block diagram depicting a thermometer code register of the type included in the writing current circuit depicted in FIG. 3;

FIG. 5 is an output stage circuit diagram depicting one embodiment of current sources included in the writing current circuit depicted in FIG. 3; and FIG. 6 is an output stage circuit diagram depicting a preferred embodiment of current sources included in the writing current circuit depicted in FIG. 3.

BEST MODE FOR CARRYING OUT THE INVENTION

The block diagram of FIG. 3 illustrates a writing current circuit 42 in accordance with the present invention that is adapted for inclusion in an IC. The writing current circuit 42 includes, in the specific embodiment depicted in FIG. 3, six (6) thermometer code registers 52a-52f. Via the writing control bus 44, the control processor 14 stores into each of the thermometer code registers 52 a numerical value which specifies a particular quantity of electrical current which the writing current circuit 42 may supply to the laser diode 34. During digital data recording, a thermometer code transfer bus 56 receives a numerical value from a selected one of the thermometer code registers 52a-52f that the writing current circuit 42 stores into a current control register 58. Serial digital data received by the writing current circuit 42 via the recorded data bus 46 specifies a sequence in which specific thermometer code registers 52 supply their respective numerical values to the thermometer code transfer bus 56 for supplying a particular electrical current waveform to the laser diode 34. Accordingly, the control processor 14 sends digital data via signal lines included in the recorded data bus 46 for selecting a specific one of the thermometer code registers 52a-52f for supplying its numerical value to the thermometer code transfer bus 56 beginning at a specific instant in time, and then subsequently selecting another of the thermometer code registers 52a-52f for supplying its numerical value to the thermometer code transfer bus 56 beginning at a subsequent instant in time. The thermometer code registers 52a-52f, the thermometer code transfer bus 56 and current control register 58 are configured so that all bits in each successive numerical value transferred across the thermometer code transfer bus 56 are stored into the current control register 58 as near to simultaneously as practicable.

In the presently preferred embodiment of the writing current circuit 42, sixty-four (64) separate current sources 62, only six (6) of which appear in FIG. 3, receive output signals from the current control register 58. The output signals from the current control register 58, specified by the numerical value of the thermometer code then present in the current control register 58, activate or deactivate individual current sources 62 which supply their combined electrical current to the current output line 48. In this way, during the recording of each bit of digital data, the current control register 58 receives and stores a sequence of thermometer code numerical values that cause the writing current circuit 42 to supply the laser diode 34 with an electrical current having a specific waveform that is specified by data loaded into the writing current circuit 42 by the control processor 14.

Because the specific waveform that the writing current circuit 42 supplies to the laser diode 34 varies depending upon the location of the spot 36 along the spiral track 38, as recording proceeds from the outer region of the track 38 to the inner region the control processor 14 must change the numerical value of thermometer codes stored in the thermometer code registers 52a-52f dynamically without disturbing digital data recording. Thus, as illustrated in FIG. 4 each of the thermometer code registers 52a-52f is, in fact, preferably a logical register that includes two (2) physical registers $52_1$ and $52_2$. During recording of digital data, only the numerical temperature code stored in one of the registers $52_1$ or $52_2$, for example register $52_1$, is available for transfer onto the thermometer code transfer bus 56. Conversely, if the register $52_1$ may be transferred onto the thermometer code transfer bus 56 then the control processor 14 may store a new temperature code value only into the register $52_2$. Immediately after the control processor 14 stores a new temperature code value into one of the registers $52_1$ or $52_2$, only that value may be transferred onto the thermometer code transfer bus 56, and the register $52_1$ or $52_2$ whose data was previously transferrable onto the thermometer code transfer bus 56 becomes available for storing the next temperature code value. Arranged in this way, the control processor 14 may store a new temperature code value into any of the thermometer code registers 52a-52f at any time without disturbing the electrical current which the writing current circuit 42 is then supplying to the current output line 48.

Each current source 62 may include an output stage of the type depicted in the circuit diagram of FIG. 5. Each current source 62 receives voltage common cathode ("VCC") and ground ("VEE") electrical power respectively via a VCC power line 102 and a VEE power line 104. Each current source 62 also receives via a current reference signal line 106 an adjustable current reference voltage signal VG_IREF that is supplied by a voltage reference circuit included in the IC, not illustrated in any of the FIGs. Data supplied by the control processor 14 to the voltage reference circuit controls the voltage of the VG_IREF signal. Each bit in the current control register 58 supplies a single on-off digital signal to each of the current sources 62 included in the writing current circuit 42 via a DRV signal line 108.

The current source 62 is preferably fabricated as part of a complementary metal oxide silicon ("CMOS") IC. As is well known to those skilled in the art of designing CMOS ICs, such ICs include both N-MOS and P-MOS transistors. For the CMOS IC depicted in FIG. 5, the N-MOS transistors are preferably fabricated directly on a silicon semiconductor substrate that contains a p-type dopant material. Alternatively, the P-MOS transistors are formed at wells of semiconductor material which during CMOS IC fabrication are established by placing n-type dopant material into the p-type substrate. Thus, the dopant material used in forming wells for P-MOS transistors in CMOS ICs is complementary to the dopant material of the ICs' substrate. For this type of CMOS IC, the well of n-type semiconductor material established in the p-type substrate for forming P-MOS transistors is frequently referred to as an n-well.

Within each current source 62, a gate of an N-MOS transistor 112 receives the voltage signal VG_IREF present on the current reference signal line 106. A source and substrate of the N-MOS transistor 112 connect to the VEE power line 104. A drain of the N-MOS transistor 112 connects to a drain of a P-MOS transistor 114. A source and n-well of the P-MOS transistor 114 connect to the VCC power line 102. The drains both of the N-MOS transistor 112 and of the P-MOS transistor 114 connect to a gate of a P-MOS transistor 116. A source of the P-MOS transistor 116 connects both to the gate of the P-MOS transistor 114 and to a drain of a P-MOS transistor 118. A gate of the P-MOS transistor 118 connects to the VEE power line 104 while the source of the P-MOS transistor 118 and the n-wells of both P-MOS transistors 118, 116 connect to the VCC power line 102. A drain of the P-MOS transistor 116 connects to a drain of an N-MOS transistor 122. A gate of the N-MOS transistor 122 connects to the VCC power line 102 while the source and substrate of the N-MOS transistor 122 connect to the VEE power line 104.

Configured in this way with the current reference voltage signal VG_IREF applied to the gate of the N-MOS transistor 112, the N-MOS transistor 112 operates as a constant current sink for current flowing through the P-MOS transistor 114 from the VCC power line 102. The series connected P-MOS transistor 114 and N-MOS transistor 112 together with the series connected P-MOS transistor 118, P-MOS transistor 116 and N-MOS transistor 122 establish a constant reference voltage $V_{REF}$ at the series connected drains of the N-MOS transistor 112 and P-MOS transistor 114 and the gate of the P-MOS transistor 116. Connection of the source of the P-MOS transistor 116 to the gate of the P-MOS transistor 114 establishes a feedback circuit for controlling and stabilizing the reference voltage $V_{REF}$.

In addition to being applied to the gate of the P-MOS transistor 116, the constant reference voltage $V_{REF}$ is also applied to a gate of a P-MOS transistor 132. A source of the P-MOS transistor 132 connects to a drain of a P-MOS transistor 134. A gate of the P-MOS transistor 134 connects to the VEE power line 104 while the source of the P-MOS transistor 134 and the n-wells of both P-MOS transistors 134, 132 connect to the VCC power line 102. A drain of the P-MOS transistor 132 connects to a drain of an N-MOS transistor 136. A gate of the N-MOS transistor 136 connects to the DRV signal line 108 while the source and substrate of the N-MOS transistor 136 connect to the VEE power line 104.

Configured in this way, when the on-off digital signal applied to the DRV signal line 108 by one of the bits in the current control register 58 turns the N-MOS transistor 136 on, an electrical current flows through the series connected P-MOS transistors 134, 132 and N-MOS transistor 136. Conversely, when the on-off digital signal applied to the DRV signal line 108 by one of the bits in the current control register 58 turns the N-MOS transistor 136 off, no electrical current flows through the series connected P-MOS transistors 134, 132 and N-MOS transistor 136.

Furthermore, arranged in the configuration described thus far, the P-MOS transistor 118 and the P-MOS transistor 134 are in a current mirror relationship, and the P-MOS transistor 116 and the P-MOS transistor 132 are also in a current mirror relationship. Arranging a pair of MOS transistors in a current mirror relationship permits setting a ratio for electrical current flowing through the pair of transistors based upon a size ratio of the two transistors. For the configuration described thus far, the size ratio of the P-MOS transistors 116, 132 is preferably the same as the size ratio of the P-MOS transistors 118, 134, thus the gate-source voltages Vgs of the P-MOS transistors 116, 132 are equal. Since the same voltage $V_{ref}$ is present on the gates of the P-MOS transistors 116, 132, presuming that as preferred the size ratio of the P-MOS transistors 118, 134 is the same as the size ratio of the P-MOS transistors 116, 132, then the voltages at the sources of the P-MOS transistors 116, 132 are identical.

The series connected drain and source of the P-MOS transistors 134, 132 also connect both to a drain of P-MOS transistor 138, and to a gate of a P-MOS transistor 142. The sources and the n-wells of both P-MOS transistors 138, 142 connect to the VCC power line 102. The drain of the P-MOS transistor 142 connects to the current output line 48. Similar to the N-MOS transistor 136, the gate of the P-MOS transistor 132 connects to the DRV signal line 108.

Configured in this way, when the on-off digital signal applied to the DRV signal line 108 by one of the bits in the current control register 58 turns the P-MOS transistor 138 on simultaneously turning the N-MOS transistor 136 off, voltage at the gate of the P-MOS transistor 142 becomes that present on the VCC power line 102, i.e. the same as the voltage at the source of the P-MOS transistor 142, and no electrical current flows through the P-MOS transistor 142 from the VCC power line 102 to the current output line 48. Conversely, when the on-off digital signal applied to the DRV signal line 108 by one of the bits in the current control register 58 turns the P-MOS transistor 138 off simultaneously turning the N-MOS transistor 136 on, voltage at the gate of the P-MOS transistor 142 becomes that present at the sources of the P-MOS transistors 116, 132, and electrical current then flows through the P-MOS transistor 142 from the VCC power line 102 to the current output line 48. During operation of the circuit depicted in FIG. 5, the N-MOS transistor 122 acts to balance the voltages between the drains of the P-MOS transistors 116, 132 so that while the P-MOS transistor 138 is turned off and the N-MOS transistor 136 is turned on the voltage at the gates of P-MOS transistors 114, 142 are identical. Also, while the P-MOS transistor 138 is turned off and the N-MOS transistor 136 is turned on the current reference voltage signal VG_IREF applied to the gate of the N-MOS transistor 112 controls how much electrical current the current source 62 supplies via the current output line 48 to the laser diode 34.

Furthermore, arranged in the configuration depicted in FIG. 5, the pair of P-MOS transistors 114, 142 are in a current mirror relationship. Thus, the ratio of electrical current flowing through the P-MOS transistors 114, 142 is determined by a size ratio of the P-MOS transistors 114, 142. In this way, the size ratio of the P-MOS transistors 114, 142 determines how much electrical current each of the current sources 62 supplies to the current output line 48 when bits in the current control register 58 turn on the P-MOS transistor 142 included in each of the current sources 62 of the writing current circuit 42.

While each current source 62 may include an output stage of the type depicted in FIG. 5, in the preferred embodiment of the writing current circuit 42 each current source 62 includes an output stage of the type depicted in the circuit diagram of FIG. 6. Those elements depicted in FIG. 6 that are common to the current source 62 illustrated in FIG. 5 carry the same reference numeral distinguished by a prime ("'") designation.

The output stage depicted in FIG. 6 is similar to that depicted in FIG. 5 in receiving an adjustable current reference signal Voltage Reference Negative ("VREFN") via a negative current reference signal line 206 which is similar to the current reference voltage signal VG_IREF depicted in FIG. 5. However, the output stage depicted in FIG. 6 differs from that depicted in FIG. 5 by receiving an adjustable current reference signal Voltage Reference Positive ("VREFP") via a negative current reference signal line 208. In the output stage depicted in FIG. 6, the current reference signal VREFP is supplied to gates both of the P-MOS transistor 118' and of the P-MOS transistor 134' rather than those gates being connected to the VEE power line 104 as in the output stage depicted in FIG. 5. A complementary voltage reference circuit included in the IC, not illustrated in any of the FIGs., supplies the current reference signals VREFN and VREFP to each of the current sources 62 included in the writing current circuit 42. Similar to the output stage depicted in FIG. 5, data supplied by the control processor 14 to the complementary voltage reference circuit controls the voltages of the VREFN and VREFP signals.

The output stage depicted in FIG. 6 further differs from that depicted in FIG. 5 by including a first resistor 212 connected between the source of the N-MOS transistor 112' and the VEE power line 104'. Also, a second resistor 214 connects between the n-well of the P-MOS transistor 142' and the VCC power line 102'. Lastly, the output stage depicted in FIG. 6 differs from that depicted in FIG. 5 by including a third resistor 222 and a capacitor 224 that connect in series between the VCC power line 102' and the junction of the drains respectively of the N-MOS transistor 112' and P-MOS transistor 114' and the gates respectively of the P-MOS transistor 116' and P-MOS transistor 132'. The resistors 212, 214 and 222 are approximately 100 ohms, and the capacitor 224 is approximately 5 pico-farads.

Adding the current reference signal VREFP for controlling operation of the P-MOS transistor 118' and the P-MOS transistor 134' permits adjusting the charging current supplied to the current output line 48 by the P-MOS transistor 142' by varying the voltage VREFP. In this way it becomes possible for the writing current circuit 42 to provide the same rise time and same overshoot for electrical current supplied to the laser diode 34 when the P-MOS transistor 138 initially turns off and the N-MOS transistor 136 initially turns on regardless of power level supplied by the current source 62. Addition of the resistor 212 improves the linearity of the current mirror relationship between the P-MOS transistor 114' and the P-MOS transistor 142' across a wider power level range. The resistor 214 in combination with the inherent source to n-well parasitic capacitance of the P-MOS transistor 142 form an embedded low pass filter at the output of the current source 62. The presence of this embedded low pass filter at the output of the current source 62 tends to reduce overshoot and undershoot in the current which the P-MOS transistor 142 supplies to the current output line 48. Lastly, addition of the series. connected resistor 222 and capacitor 224 reduces the possibility that the feedback circuit formed by the P-MOS transistor 114' and the P-MOS transistor 116' may oscillate during high speed switching.

INDUSTRIAL APPLICABILITY

Depending upon specific recording conditions, the electrical current which the writing current circuit 42 in accordance with the present invention supplies to the laser diode 34 when recording onto a DVD at 16× increases from a nominal value of approximately ten milliamperes ("ma") at time $t_0$ in FIG. 2 to several hundred ma at time $t_1$, a time interval of approximately one-half (0.5) nanosecond. When recording onto a DVD at 16×, the maximum electrical current supplied to the laser diode 34, $I_P$, may be as great as 500 ma.

Although the present invention has been described in terms of the presently preferred embodiment, it is to be understood that such disclosure is purely illustrative and is not to be interpreted as limiting. For example, a writing current circuit 42 in accordance with the present invention may include more or fewer than six (6) thermometer code registers 52. Similarly, a writing current circuit 42 in accordance with the present invention may include more or fewer than sixty-four (64) current sources 62. While the current source 62 preferably employs a P-MOS transistor 142 for supplying electrical current to the laser diode 34 via the current output line 48, a current source 62 in accordance with the present invention may instead use an N-MOS transistor therefor. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. A writing current circuit (42) adapted for supplying a controlled electrical current to a laser diode (34) included in a drive (10), the drive (10) being adapted for swiftly recording digital data onto a Digital Video Disc ("DVD") (16), the writing current circuit (42) receiving from a control processor (14) included in the drive (10) both:
    a. write control digital data via a writing control bus (44) which interconnects the writing current circuit (42) and the control processor (14); and
    b. serial digital data to be recorded on a DVD (16) via a recorded data bus (46) which also interconnects the writing current circuit (42) and the control processor (14), the writing current circuit (42) comprising:
    a plurality of thermometer code registers (52) each of which is adapted for storing a numerical value which specifies a particular quantity of electrical current which the writing current circuit (42) may supply to the laser diode (34), the thermometer code registers (52) respectively receiving the stored numerical values from the control processor (14) via the writing control bus (44);
    a current control register (58) which is adapted for receiving a numerical value from a selected one of the thermometer code registers (52) via a thermometer code transfer bus (56) which interconnects the current control register (58) with all of the thermometer code registers (52), serial digital data received by the thermometer code registers (52) via the recorded data bus (46) specifying a sequence in which individual thermometer code registers (52) supply respective numerical values to the current control register (58) via the thermometer code transfer bus (56) whereby the writing current circuit (42) supplies a particular electrical current waveform to the laser diode (34); and
    a plurality of separate current sources (62) each of which receives a single output signal from the current control register (58), the output signal respectively received by each current source (62) from the current control register (58):
    a. when in a first state activating the receiving current source (62) for supplying a particular quantity of electrical current to the laser diode (34); and
    b. when in a second state deactivating the receiving current source (62) for supplying the particular quantity of electrical current to the laser diode (34).

2. The writing current circuit (42) of claim 1 wherein each of the thermometer code registers (52) is a logical register that includes at least pair of physical registers ($52_1$, $52_2$), at any instant in time:
    a. a first of the physical registers ($52_1$, $52_2$) storing the numerical value which is transferrable from the logical thermometer code register (52) to the thermometer code transfer bus (56); and
    b. a second of the physical registers ($52_1$, $52_2$) being available for storing a new numerical value received from the control processor (14) via the writing control bus (44); whereby each thermometer code register (52) is adapted for supplying the numerical value to the thermometer code transfer bus (56) from the first physical register ($52_1$, $52_2$) while the second physical register ($52_1$, $52_2$) concurrently receives the new numerical value from the control processor (14).

3. The writing current circuit (42) of claim 1 wherein each current source (62), in addition to receiving a single output signal from the current control register (58), also receives both:
    a. a first current reference voltage signal which controls how much electrical current the current source (62) supplies to the laser diode (34) when the single output signal received by the current source (62) from the current control register (58) is in the first state; and
    b. a second current reference voltage signal for controlling the charging electrical current supplied to the laser diode (34) by current source (62) when the single output signal received by the current source (62) from the current control register (58) initially enters the first state, whereby the writing current circuit (42) is adapted for providing the same rise time and same overshoot for electrical current supplied to the laser diode (34) regardless of how much electrical current the current source (62) supplies to the laser diode (34).

4. The writing current circuit (42) of claim 3 wherein digital data from the control processor (14) adjusts both the first current reference voltage signal and the second current reference voltage signal.

5. The writing current circuit (42) of claim 1 wherein each current source (62) includes at least one metal oxide silicon ("MOS") transistor (142') having a gate, a source and a drain, electrical current for the laser diode (34) flowing through the MOS transistor (142') between the source and the drain thereof, the MOS transistor (142') including a well of semiconductor material formed with a first dopant material, the well of semiconductor material being established in a substrate of semiconductor material containing a dopant material which complements the first dopant material, the current source (62) further including a resistor connected between a source of electrical power for the writing current circuit (42) and the well of the MOS transistor (142'), whereby the resistor in combination with inherent source to well parasitic capacitance of the MOS transistor (142') form an embedded low pass filter.

6. A method for operating a writing current circuit (42) that is adapted for supplying a controlled electrical current to a laser diode (34) included in a drive (10), the drive (10) being adapted for swiftly recording digital data onto a DVD (16), the method comprising the steps of:
    the writing current circuit (42) providing a plurality of thermometer code registers (52) for respectively receiving and storing a numerical value which specifies a particular quantity of electrical current which the writing current circuit (42) may supply to the laser diode (34);
    the writing current circuit (42) receiving from a control processor (14) included in the drive (10) both:
    a. write control digital data including numerical values which are received into and stored in the thermometer code registers (52); and
    b. serial digital data to be recorded on a DVD (16);
    the writing current circuit (42) further providing a current control register (58) for receiving a numerical value from a selected one of the thermometer code registers (52);
    the writing current circuit (42) receiving from the control processor (14) serial digital data for specifying a sequence in which individual thermometer code registers (52) supply respective numerical values to the current control register (58) whereby the writing current circuit (42) supplies a particular electrical current waveform to the laser diode (34); and the writing current circuit (42) also providing a plurality of separate current sources (62) for respectively receiving a single output signal from the current control register (58), the output signal respectively received by each current source (62):

a. when in a first state activating the receiving current source (62) for supplying a particular quantity of electrical current to the laser diode (34); and b. when in a second state deactivating the receiving current source (62) for supplying the particular quantity of electrical current to the laser diode (34).

7. The method of claim 6 wherein each of the thermometer code registers (52) is a logical register that includes at least pair of physical registers (52$_1$, 52$_2$), the method further comprising the steps of at any instant in time:

a. a first of the physical registers (52$_1$, 52$_2$) storing the numerical value which is transferrable from the logical thermometer code register (52) to the current control register (58); and b. a second of the physical registers (52$_1$, 52$_2$) being capable of receiving from the control processor (14) and storing a new numerical value;

whereby each thermometer code register (52) is adapted for supplying the numerical value to the current control register (58) from the first physical register (52$_1$, 52$_2$) while the second physical register (52$_1$, 52$_2$) is concurrently receiving the new numerical value from the control processor (14).

8. The method of claim 6 wherein each current source (62), in addition to receiving a single output signal from the current control register (58), receiving both:

a. a first current reference voltage signal which controls how much electrical current the current source (62) supplies to the laser diode (34) when the single output signal received by the current source (62) from the current control register (58) is in the first state; and b. a second current reference voltage signal for controlling the charging electrical current supplied to the laser diode (34) by current source (62) when the single output signal received by the current source (62) from the current control register (58) initially enters the first state, whereby the writing current circuit (42) provides the same rise time and same overshoot for electrical current supplied to the laser diode (34) regardless of how much electrical current the current source (62) supplies to the laser diode (34).

9. The method of claim 8 wherein the control processor (14) supplies digital data for adjusting both the first current reference voltage signal and the second current reference voltage signal.

10. The method of claim 6 wherein each current source (62) includes at least one MOS transistor (142') having a gate, a source and a drain, electrical current for the laser diode (34) flowing through the MOS transistor (142') between the source and the drain thereof, the MOS transistor (142') including a well of semiconductor material formed with a first dopant material, the well of semiconductor material being established in a substrate of semiconductor material containing a dopant material which complements the first dopant material, the method further comprising the step of forming an embedded low pass filter in the current source (62) by including therein a resistor connected between a source of electrical power for the writing current circuit (42) and the well of the MOS transistor (142'), whereby the resistor in combination with inherent source to well parasitic capacitance of the MOS transistor (142') provides the embedded low pass filter.

* * * * *